United States Patent [19]
Takahashi et al.

[11] Patent Number: 4,672,070
[45] Date of Patent: Jun. 9, 1987

[54] FUNGICIDAL N-PYRIDINYLAMIDE DERIVATIVES

[75] Inventors: Junya Takahashi, Hyogo; Hiroshi Noguchi; Yukio Oguri, both of Toyonaka; Shigeo Yamamoto, Kawanishi; Toshiro Kato, Takarazuka; Katsuzo Kamoshita, Osaka, all of Japan

[73] Assignee: Sumitomo Chemical Company, Limited, Osaka, Japan

[21] Appl. No.: 823,991

[22] Filed: Jan. 29, 1986

[30] Foreign Application Priority Data

Jan. 30, 1985 [JP] Japan .................................. 60-17176
Feb. 5, 1985 [JP] Japan .................................. 60-20653

[51] Int. Cl.$^4$ .................... A01N 43/40; C07D 213/75
[52] U.S. Cl. ...................................... 514/346; 548/292
[58] Field of Search ......................... 548/292; 514/346

[56] References Cited

U.S. PATENT DOCUMENTS 3,376,309  4/1968  Foster et al. .................... 546/292

Primary Examiner—Henry R. Jiles
Assistant Examiner—Kurt G. Briscoe
Attorney, Agent, or Firm—Birch, Stewart, Kolasch & Birch

[57] ABSTRACT

A compound of the formula:

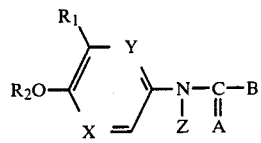

useful as a fungicidal agent against phytopathogenic fungi, particularly their strains resistance to benzimidazole or thiophanate fungicides and/or cyclic imide fungicides.

11 Claims, No Drawings

FUNGICIDAL N-PYRIDINYLAMIDE DERIVATIVES

This invention relates to fungicidal pyridine derivatives.

Benzimidazole and thiophanate fungicides such as Benomyl (methyl 1-(butylcarbamoyl)benzimidazol-2-ylcarbamate), Fubelidazol (2-(2-furyl)benzimidazole), Thiabendazole (2-(4-thiazolyl)benzimidazole), Carbendazim (methyl benzimidazol-2-ylcarbamate), Thiophanate-methyl (1,2-bis(3-methoxycarbonyl-2-thioureido)benzene), Thiophanate (1,2-bis(3-ethoxycarbonyl-2-thioureido)benzene), 2-(O,S-dimethylphosphorylamino)-1-(3'-methoxycarbonyl-2'-thioureido)benzene and 2-(O,O-dimethylthiophosphorylamino)-1-(3'-methoxycarbonyl-2'-thioureido)benzene are known to show an excellent fungicidal activity against various plant pathogenic fungi, and they have been widely used as agricultural fungicides since 1970. However, their continuous application over a long period of time provides phytopathogenic fungi with tolerance to them, whereby their plant disease-preventive effect is much lowered. Further, the fungi which gained tolerance to certain kinds of benzimidazole or thiophanate fungicides also show considerable tolerance to some other kinds of benzimidazole or thiophanate fungicides. Thus, they are apt to obtain cross-tolerance. Therefore, if any material decrease of their plant disease-preventive effect in certain fields is observed, their application to such fields has to be discontinued. But, it is often observed that the density of drug-resistant organisms is not decreased even long after the discontinuation of the application. Although other kinds of fungicides have to be employed in such case, only few are so effective as benzimidazole or thiophanate fungicides in controlling various phytopathogenic fungi. Benzimidazole and thiophanate fungicides will be hereinafter referred to as "benzimidazole thiophanate fungicides".

Cyclic imide fungicides such as Procymidone (3-(3',5'-dichlorophenyl)-1,2-dimethylcyclopropane-1,2-dicarboximide), Iprodione (3-(3',5'-dichlorophenyl)-1-isopropylcarbamoylimidazolidine-2,4-dione), Vinchlozolin (3-(3',5'-(dichlorophenyl)-5-methyl-5-vinyloxazolidin-2,4-dione), ethyl (RS)-3-(3',5'-dichlorophenyl)-5-methyl-2,4-dioxooxazolidine-5-carboxylate, etc., which are effective against various plant diseases, particularly those caused by Botrytis cinerea, have the same defects as previously explained with respect to the benzimidazole thiophanate fungicides.

In C.R. Acad. Sc. Paris, t. 289, S'erie D, pages 691–693 (1979), it is described that such herbicides as Barban (4-chloro-2-butynyl N-(3-chlorophenyl)carbamate), Chlorobufam (1-methyl-2-propynyl N-(3-chlorophenyl)carbamate), Chlorpropham (isopropyl N-(3-chlorophenyl)carbamate) and Propham (isopropyl N-phenylcarbamate) exhibit a fungicidal activity against certain organisms tolerant to some of benzimidazole thiophanate fungicides. However, their fungicidal activity against the drug-resistant fungi is not strong enough, and hence, practically they can not be used as fungicides.

As a result of the study seeking a new type of fungicides, it has now been found that pyridine derivatives of the formula:

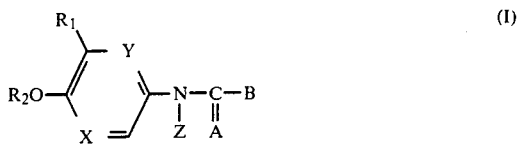

wherein
either one of X and Y is a methine group and the other is a nitrogen atom;
$R_1$ is a halogen atom or a group of the formula: —$WR_3$ or —$NHCOOR_4$ (in which W is an oxygen atom or a sulfur atom, $R_3$ is a lower alkyl group, a lower alkenyl group, a lower alkynyl group, a lower haloalkyl group or a lower alkoxy(lower)alkyl group and $R_4$ is a lower alkyl group);
$R_2$ is a lower alkyl group, a lower alkenyl group, a lower alkynyl group, a lower haloalkyl group or a lower alkoxy(lower)alkyl group;
Z is a hydrogen atom, a lower alkyl group, a lower alkenyl group, a lower alkynyl group, a lower alkoxycarbonyl(lower)alkyl group or a group of the formula: —$COR_5$ or —$SR_6$ (in which $R_5$ is a lower alkyl group, a cyclo(lower)alkyl group or a phenyl group and $R_6$ is a lower alkyl group, a phenyl group or a lower alkoxycarbonyl group);
A is an oxygen atom or a sulfur atom; and
B is a lower alkyl group, a lower alkenyl group, a cyclo(lower)alkyl group, a phenyl group or a group of the formula: —$W'R_7$ (in which W' is an oxygen atom or a sulfur atom and $R_7$ is a lower alkyl group, a lower alkenyl group, a lower alkynyl group, a halo(lower)alkenyl group, a halo(lower)alkynyl group, a cyclo(lower)alkyl group, a phenyl group optionally substituted with halogen or a lower alkyl group substituted with at least one member selected from the group consisting of halogen, cyano, phenyl, cyclo(lower)alkyl or lower alkoxy), show an excellent fungicidal activity against plant pathogenic fungi which have developed resistance to benzimidazole and thiophanate fungicides and/or cyclic imide fungicides. It is notable that their fungicidal potency against the organisms tolerant to benzimidazole and thiophanate fungicides and/or cyclic imide fungicides (hereinafter referred to as "drug-resistant fungi" or "drug-resistant strains") is much higher than that against the organisms sensitive to benzimidazole and thiophanate fungicides and/or cyclic imide fungicides (hereinafter referred to as "drug-sensitive fungi" or "drug-sensitive strains").

The term "lower" used hereinabove and hereinafter in connection with organic radicals or compounds indicates that such radicals or compounds each have not more than 6 carbon atoms.

Typical examples of the pyridine derivatives (I) are shown in Table 1.

TABLE 1

$$\begin{array}{c} R_1 \\ | \\ R_2O-C=C-Y \\ | \quad \quad \| \\ X \quad \quad N-C-B \\ \quad \quad | \quad \| \\ \quad \quad Z \quad A \end{array} \quad (I)$$

| R$_1$ | R$_2$ | X | Y | Z | A | B |
|---|---|---|---|---|---|---|
| Br | C$_2$H$_5$ | CH | N | H | O | OCH$_3$ |
| Br | C$_2$H$_5$ | CH | N | H | O | O(i)C$_3$H$_7$ |
| OC$_2$H$_5$ | C$_2$H$_5$ | CH | N | H | O | OCH$_3$ |
| OC$_2$H$_5$ | C$_2$H$_5$ | CH | N | H | O | OC$_2$H$_5$ |
| SC$_2$H$_5$ | C$_2$H$_5$ | CH | N | H | O | O(i)C$_3$H$_7$ |
| OC$_2$H$_5$ | C$_2$H$_5$ | CH | N | H | O | O(i)C$_3$H$_7$ |
| —NHCOOCH$_3$ | C$_2$H$_5$ | N | CH | H | O | OCH$_3$ |
| OC$_2$H$_5$ | C$_2$H$_5$ | CH | N | H | O | C$_2$H$_5$ |
| OC$_2$H$_5$ | C$_2$H$_5$ | CH | N | H | O | 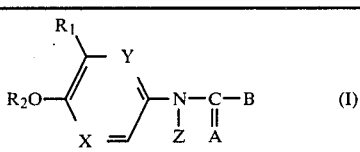 |
| OC$_2$H$_5$ | C$_2$H$_5$ | CH | N | H | O | SC$_2$H$_5$ |
| OC$_2$H$_5$ | C$_2$H$_5$ | CH | N | H | O | —OCH$_2$CH=CH$_2$ |
| —SCH$_2$CH=CH$_2$ | —CH$_2$CH=CH$_2$ | CH | N | H | O | O(i)C$_3$H$_7$ |
| OC$_2$H$_5$ | —CH$_2$C≡CH | CH | N | H | O | O(i)C$_3$H$_7$ |
| OCH$_3$ | —CH$_2$CH$_2$F | CH | N | H | O | O(i)C$_3$H$_7$ |
| OCH$_3$ | —CH$_2$CH$_2$OCH$_3$ | CH | N | H | O | O(i)C$_3$H$_7$ |
| —OCH$_2$C≡CH | C$_2$H$_5$ | CH | N | H | O | O(i)C$_3$H$_7$ |
| —OCH$_2$CH$_2$Cl | C$_2$H$_5$ | CH | N | H | O | O(i)C$_3$H$_7$ |
| —OCH$_2$CH$_2$OCH$_3$ | C$_2$H$_5$ | CH | N | H | O | O(i)C$_3$H$_7$ |
| OC$_2$H$_5$ | C$_2$H$_5$ | CH | N | CH$_3$ | O | O(i)C$_3$H$_7$ |
| OC$_2$H$_5$ | C$_2$H$_5$ | CH | N | —CH$_2$CH=CH$_2$ | O | O(i)C$_3$H$_7$ |
| OC$_2$H$_5$ | C$_2$H$_5$ | CH | N | —CH$_2$C≡CH | O | O(i)C$_3$H$_7$ |
| OC$_2$H$_5$ | C$_2$H$_5$ | CH | N | —CHCOOCH$_3$<br>\|<br>CH$_3$ | O | O(i)C$_3$H$_7$ |
| OC$_2$H$_5$ | C$_2$H$_5$ | CH | N | —C—CH$_3$<br>\|\|<br>O | O | O(i)C$_3$H$_7$ |
| OC$_2$H$_5$ | C$_2$H$_5$ | CH | N |  | O | O(i)C$_3$H$_7$ |
| OC$_2$H$_5$ | C$_2$H$_5$ | CH | N |  | O | O(i)C$_3$H$_7$ |
| OC$_2$H$_5$ | C$_2$H$_5$ | CH | N | —SCH$_3$ | O | O(i)C$_3$H$_7$ |
| OC$_2$H$_5$ | C$_2$H$_5$ | CH | N | 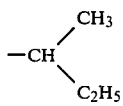 | O | O(i)C$_3$H$_7$ |
| OC$_2$H$_5$ | C$_2$H$_5$ | CH | N | —SCOOC$_2$H$_5$ | O | O(i)C$_3$H$_7$ |
| OC$_2$H$_5$ | C$_2$H$_5$ | CH | N | H | S | O(i)C$_3$H$_7$ |
| OC$_2$H$_5$ | C$_2$H$_5$ | CH | N | H | O | —CH(CH$_3$)C$_2$H$_5$ |
| OC$_2$H$_5$ | C$_2$H$_5$ | CH | N | H | O | —CH=CHCH$_3$ |
| OC$_2$H$_5$ | C$_2$H$_5$ | CH | N | H | O |  |

TABLE 1-continued

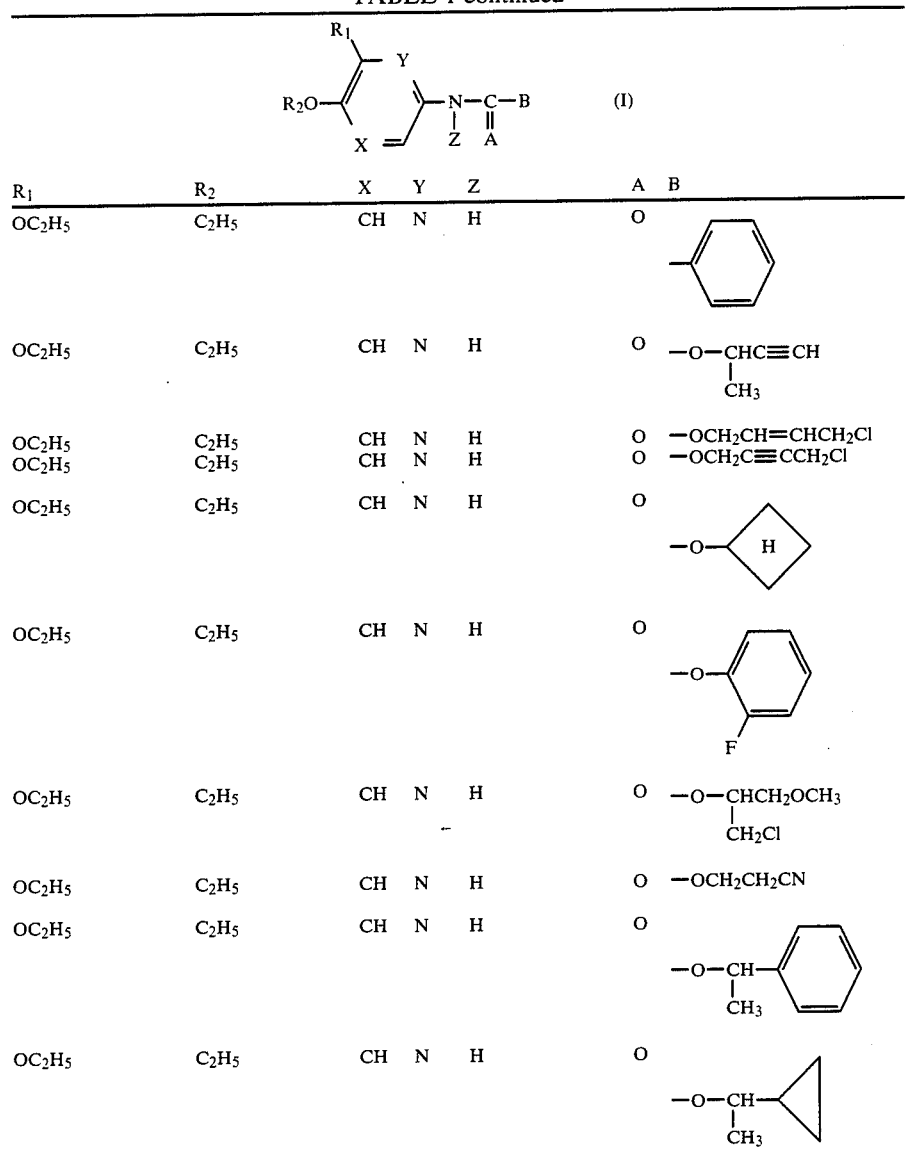

| $R_1$ | $R_2$ | X | Y | Z | A | B |
|---|---|---|---|---|---|---|
| $OC_2H_5$ | $C_2H_5$ | CH | N | H | O | ![phenyl] |
| $OC_2H_5$ | $C_2H_5$ | CH | N | H | O | $-O-\underset{CH_3}{CH}C\equiv CH$ |
| $OC_2H_5$ | $C_2H_5$ | CH | N | H | O | $-OCH_2CH=CHCH_2Cl$ |
| $OC_2H_5$ | $C_2H_5$ | CH | N | H | O | $-OCH_2C\equiv CCH_2Cl$ |
| $OC_2H_5$ | $C_2H_5$ | CH | N | H | O | $-O-\text{cyclopropyl(H)}$ |
| $OC_2H_5$ | $C_2H_5$ | CH | N | H | O | $-O-\text{(2-fluorophenyl)}$ |
| $OC_2H_5$ | $C_2H_5$ | CH | N | H | O | $-O-\underset{CH_2Cl}{CH}CH_2OCH_3$ |
| $OC_2H_5$ | $C_2H_5$ | CH | N | H | O | $-OCH_2CH_2CN$ |
| $OC_2H_5$ | $C_2H_5$ | CH | N | H | O | $-O-\underset{CH_3}{CH}-\text{phenyl}$ |
| $OC_2H_5$ | $C_2H_5$ | CH | N | H | O | $-O-\underset{CH_3}{CH}-\text{cyclopropyl}$ |

The compounds of the formula (I) are fungicidally effective against a wide scope of plant pathogenic fungi, of which examples are as follows: *Podosphaera leucotricha, Venturia inaequalis, Mycosphaerella pomi, Marssonina mali* and *Sclerotinia mali* of apple, *Phyllactinia kakicola* and *Gloeosporium kaki* of persimmon, *Cladosporium carpophilum* and *Phomopsis* sp. of peach, *Cercospora viticola, Uncinula necator, Elsinoe ampelina* and *Glomerella cingulata* of grape, *Cercospora beticola* of sugarbeet, *Cercospora arachidicola* and *Cercospora personata* of peanut, *Erysiphe graminis* f. sp. *hordei, Cercosporella herpotrichoides* and *Fusarium nivale* of barley, *Erysiphe graminis* f. sp. *tritici* of wheat, *Sphaerotheca fuliginea* and *Cladosporium cucumerinum* of cucumber, *Cladosporium fulvum* of tomato, *Corynespora melongenae* of eggplant, *Sphaerotheca humuli, Fusarium oxysporum* f. sp. *fragariae* of strawberry, *Botrytis alli* of onion, *Cercospora apii* of cerely, *Phaeoisariopsis griseola* of kidney bean, *Erysiphe cichoracearum* of tobacco, *Diplocarpon rosae* of rose, *Elsinoe fawcetti, Penicillium italicum, Penicillium digitatum* of orange, *Botrytis cinerea* of cucumber, eggplant, tomato, strawberry, pimiento, onion, lettuce, grape, orange, cyclamen, rose or hop, *Sclerotinia sclerotiorum* of cucumber, eggplant, pimiento, lettuce, celery, kidney bean, soybean, azuki bean, potato òr sunflower, *Sclerotinia cinerea* of peach or cherry, *Mycosphaerella melonis* of cucumber or melon, etc. Namely, the compounds of the formula (I) are highly effective in controlling the drug-resistant strains of said fungi.

The compounds of the formula (I) are also fungicidally effective against fungi sensitive to said known fungicides as well as fungi to which said known fungicides are ineffective. Examples of such fungi are *Pyricularia oryzae, Pseudoperonospora cubensis, Plasmopara viticola, Phytophthora infestans*, etc.

Advantageously, the compounds of the formula (I) are low toxic and have little detrimental actions on mammals, fishes and so on. Also, they may be applied to the agricultural field without causing any material toxicity to important crop plants.

In view of their excellent fungicidal properties, particularly useful are the compounds of the formula (I)

wherein X is a methine group, Y is a nitrogen atom, Z is a hydrogen atom, A is an oxygen atom, B is a lower alkyl group, a lower cycloalkyl group or a group of the formula: —WR$_3$ (in which W is an oxygen atom or a sulfur atom and R$_3$ is a lower alkyl group or a lower alkenyl group), R$_1$ is a lower alkoxy group and R$_2$ is a lower alkyl group. More preferred are the compounds of the formula (I) wherein X is a methine group, Y is a nitrogen atom, Z is a hydrogen atom, A is an oxygen atom, B is an ethyl group, a cyclopropyl group, an ethylthio group or a group of the formula: —OR$_3$ (in which R$_3$ is a methyl group, an ethyl group, an isopropyl group or an allyl group), R$_1$ is an ethoxy group and R$_2$ is an ethyl group.

The compounds (I) can be prepared by either one of the following procedures:

Procedure (a):

The compound (I) can be prepared by reacting a compound of the formula:

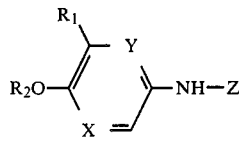 (II)

wherein X, Y, R$_1$, R$_2$ and Z are each as defined above with a compound of the formula:

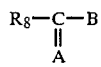 (III)

wherein A and B are each as define above and R$_8$ is a halogen atom.

The reaction is usually carried out in an inert solvent (e.g. water, benzene, toluene, xylene, diethyl ether, tetrahydrofuran, dioxane, chloroform, carbon tetrachloride, ethyl acetate, pyridine, N,N-dimethylformamide). The reaction may be performed in the existence of a base (e.g. pyridine, triethylamine, N,N-diethylaniline, sodium hydride, potassium hydroxide). If desired, a phase transfer catalyst (e.g. tetra-n-butylammonium bromide) can be used so as to obtain the compound (I) in a high yield. The reaction may be accomplished at a temperature of 0° to 150° C. within 10 hours.

The compound (II) wherein Z is a hydrogen atom can be obtained by reducing a compound of the formula:

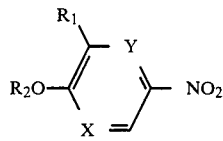 (IV)

wherein X, Y, R$_1$ and R$_2$ are each as defined above.

The reduction may be performed in an inert solvent (e.g. water, methanol, ethanol) using a reducing agent (e.g. sodium sulfide, sodium hydrosulfide). The reaction may be accomplished at a temperature of 50° C. to the boiling point of the solvent.

Alternatively, the reduction may be performed with a metal powder (e.g. iron powder, zinc powder, tin powder) in an aqueous organic or inorganic acid (e.g. acetic acid, hydrochloric acid, sulfuric acid) at a temperature of 50° to 100° C. within about 12 hours.

The reduction may be also performed in an inert solvent (e.g. ethanol, ethyl acetate) in the presence of a catalyst (e.g. platinum oxide, palladium on carbon) in hydrogen stream under a pressure of 1 to 100 atm at a temperature of 0° to 60° C. within about 12 hours.

The compound (IV) is obtainable by a per se known method [Aust.J.Chem., 34, 927–932 (1981)].

The compound (II) wherein Z is other than a hydrogen atom can be obtained by reacting a compound of the formula:

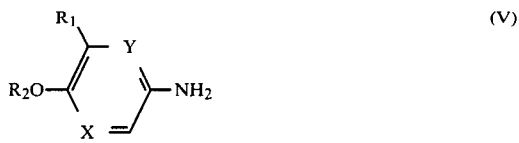 (V)

wherein X, Y, R$_1$ and R$_2$ are each as defined above with a compound of the formula:

 (VI)

wherein Z is as defined above and G is a leaving group such as halogen, tosyloxy or mesyloxy.

The reaction may be accomplished in an organic solvent (e.g. N,N-dimethylformamide, dimethylsulfoxide, tetrahydrofuran, dioxane, toluene, benzene, ether) or in a two phase medium (e.g. water and toluene or benzene) using a base (e.g. sodium hydroxide, potassium carbonate, sodium hydride, N,N-diethylaniline, pyridine). If desired, any catalyst (e.g. tetra-n-butylammonium bromide) may be used in the reaction system to accelerate the reaction. The reaction usually proceeds at a temperature of 0° to 100° C. for a period of about 12 hours.

Procedure (b):

The compound (I) wherein Z is other than hydrogen may be prepared by reacting a compound of the formula:

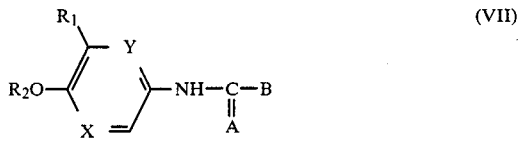 (VII)

wherein X, Y, R$_1$, R$_2$, A and B are each as defined above with the compound (VI).

The reaction is performed in the presence of an organic solvent (e.g. N,N-dimethylformamide, dimethylsulfoxide, diethyl ether, tetrahydrofuran) with a base (e.g. sodium hydride, potassium hydroxide) at a temperature of 0° to 100° C. within about 12 hours. If desired, a phase transfer catalyst such as tetrabutylammonium bromide may be in the reaction system.

A typical example for preparation of the compound (I) is illustratively shown in the following Example.

EXAMPLE 1

2-Amino-5,6-diethoxypyridine (1.83 g) and N,N-diethylaniline (1.49 g) were dissolved in ethyl acetate (30 ml). To the resultant solution, there was dropwise added isopropyl chloroformate (1.23 g) in 5 minutes under ice-cooling. The resulting mixture was allowed to stand at room temperature for 12 hours, poured into ice-water and extracted with ethyl acetate. The extract was washed with water, dried over magnesium sulfate and concentrated under reduced pressure. The residue was purified by basic alumina chromatography using a mixture of toluene and ethyl acetate as an eluent to give 2-isopropyloxycarbonylamino-5,6,-diethoxypyridine (2.24 g) in a yield of 83.5%.

In the same manner as above, the compounds of the formula (I) as shown in Table 2 can be obtained.

Examples of the liquid carriers or diluents are water, alcohols (e.g. methanol, ethanol), ketones (e.g. acetone, methylethylketone), ethers (e.g. diethyl ether, dioxane, cellosolve, tetrahydrofuran), aromatic hydrocarbons (e.g. benzene, toluene, xylene, methyl naphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, carbon tetrachloride), etc.

TABLE 2

| Compound No. | $R_1$ | $R_2$ | X | Y | Z | A | B | Physical constant |
|---|---|---|---|---|---|---|---|---|
| 1 | Br | $C_2H_5$ | CH | N | H | O | $OCH_3$ | m.p., 157.5–158.5° C. |
| 2 | Br | $C_2H_5$ | CH | N | H | O | $O(i)C_3H_7$ | m.p., 95.5–96.5° C. |
| 3 | $OC_2H_5$ | $C_2H_5$ | CH | N | H | O | $OCH_3$ | m.p., 111.5–112.5° C. |
| 4 | $OC_2H_5$ | $C_2H_5$ | CH | N | H | O | $OC_2H_5$ | m.p., 85–86° C. |
| 5 | $SC_2H_5$ | $C_2H_5$ | CH | N | H | O | $O(i)C_3H_7$ | NMR $\delta_{TMS}^{CDCl_3}$: 3.03 (q, 2H), 3.98 (q,2H), 4.94 (m, 1H), 6.90 (d,1H), 7.44 (d,1H) |
| 6 | $OC_2H_5$ | $C_2H_5$ | CH | N | H | O | $O(i)C_3H_7$ | NMR $\delta_{TMS}^{CDCl_3}$: 4.08 (q,2H), 4.35 (q,2H), 5.00 (m, 1H), 7.10 (d,1H), 7.40 (d,1H) |
| 7 | $-NHCOOCH_3$ | $C_2H_5$ | N | CH | H | O | $OCH_3$ | m.p., 136.5–137° C. |
| 8 | $OC_2H_5$ | $C_2H_5$ | CH | N | H | O | $C_2H_5$ | NMR $\delta_{TMS}^{CDCl_3}$: 2.36 (q,2H), 4.00 (q,2H), 4.30 (q, 2H), 7.05 (d,1H), 7.62 (d,1H) |
| 9 | $OC_2H_5$ | $C_2H_5$ | CH | N | H | O | cyclopropyl | NMR $\delta_{TMS}^{CDCl_3}$: 0.60–1.20 (m,5H), 4.00 (q,2H), 4.32 (q,2H), 7.04 (d, 1H), 7.60 (d,1H) |
| 10 | $OC_2H_5$ | $C_2H_5$ | CH | N | H | O | $SC_2H_5$ | NMR $\delta_{TMS}^{CDCl_3}$: 2.95 (q,2H), 4.00 (q,2H), 4.30 (q, 2H), 7.05 (q,1H), 7.40 (d,1H) |
| 11 | $OC_2H_5$ | $C_2H_5$ | CH | N | H | O | $-OCH_2CH=CH_2$ | NMR $\delta_{TMS}^{CDCl_3}$: 4.00 (q,2H), 4.30 (q,2H), 4.62 (d, 2H), 5.00–6.30 (m, 3H), 7.05 (d,1H) 7.35 (d,1H) |

In the practical usage of the compounds (I) as fungicides, they may be applied as such or in a formulation form such as dusts, wettable powders, oil sprays, emulsifiable concentrates, tablets, granules, fine granules, aerosols or flowables. Such formulation form can be formulated in a conventional manner by mixing at least one of the compounds (I) with an appropriate solid or liquid carrier(s) or diluent(s) and, if necessary, an appropriate adjuvant(s) (e.g. surfactants, adherents, dispersants, stabilizers) for improving the dispersibility and other properties of the active ingredient.

Examples of the solid carriers or diluents are botanical materials (e.g. flour, tobacco stalk powder, soybean powder, walnut-shell powder, vegetable powder, saw dust, bran, bark powder, cellulose powder, vegetable extract residue), fibrous materials (e.g. paper, corrugated cardboard, old rags), synthetic plastic powders, clays (e.g. kaolin, bentonite, fuller's earth), talcs, other inorganic materials (e.g. pyrophyllite, sericite, pumice, sulfur powder, active carbon) and chemical fertilizers (e.g. ammonium sulfate, ammonium phosphate, ammonium nitrate, urea, ammonium chloride).

Examples of the surfactants are alkyl sulfuric esters, alkyl sulfonates, alkylaryl sulfonates, polyethylene glycol ethers, polyhydric alcohol esters, etc. Examples of the adherents and dispersants may include casein, gelatin, starch powder, carboxymethyl cellulose, gum arabic, alginic acid, lignin, bentonite, molasses, polyvinyl alcohol, pine oil and agar. As the stabilizers, there may be used PAP (isopropyl acid phosphate mixture), tricresyl phosphate (TCP), tolu oil, epoxydized oil, various surfactants, various fatty acids and their esters, etc.

The foregoing formulations generally contain at least one of the compounds (I) in a concentration of about 1 to 95% by weight, preferably of 2.0 to 80% by weight. By using the formulations, the compounds (I) are generally applied in such amounts as 2 to 100 g per 10 are.

When only the drug-resistant strains of phytopathogenic fungi are present, the compounds (I) may be used alone. However, when the drug-sensitive strains are present together with the drug-resistant strains, their alternate use with benzimidazole thiophanate fungicides and/or cyclic imide fungicides or their combined use with benzimidazole thiophanate fungicides and/or cyclic imide fungicides is favorable. In such alternate or combined use, each active ingredient may be employed as such or in conventional agricultural formulation forms. In case of the combined use, the weight proportion of the compound (I) and the benzimidazole thiophanate fungicide and/or the cyclic imide fungicide may be from about 1:0.1 to 1:10.0.

Typical examples of the benzimidazole thiophanate fungicides and the cyclic imide fungicides are shown in Table 3.

TABLE 3

| Compound | Structure | Name |
|---|---|---|
| A | 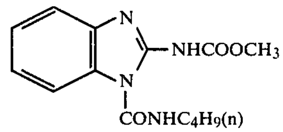 | Methyl 1-(butylcarbamoyl)benzimidazol-2-ylcarbamate |
| B | 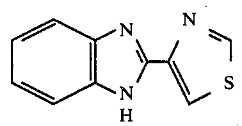 | 2-(4-Thiazolyl)benzimidazole |
| C | 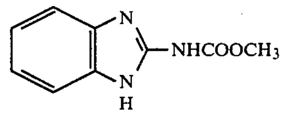 | Methyl benzimidazol-2-ylcarbamate |
| D | 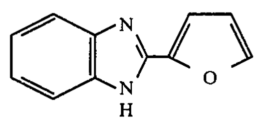 | 2-(2-Furyl)benzimidazole |
| E | 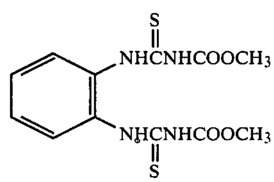 | 1,2-Bis(3-methoxycarbonyl-2-thioureido)benzene |
| F | 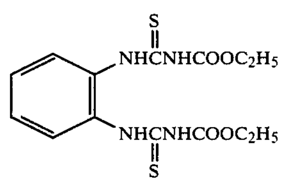 | 1,2-Bis(3-ethoxycarbonyl-2-thioureido)benzene |
| G | 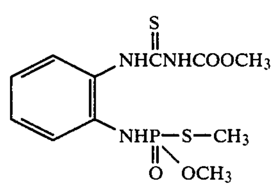 | 2-(O,S—Dimethylphosphorylamino)-1-(3'-methoxycarbonyl-2'-thioureido)benzene |
| H | 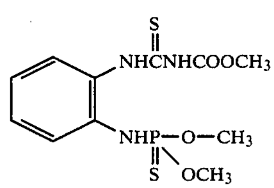 | 2-(O,O—Dimethylthiophosphorylamino)-1-(3'-methoxycarbonyl-2'-thioureido)benzene |
| I | 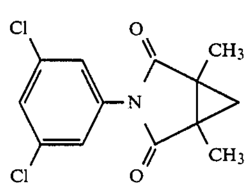 | N—(3',5'-Dichlorophenyl)-1,2-dimethylcyclopropane-1,2-dicarboximide |

TABLE 3-continued

| Compound | Structure | Name |
|---|---|---|
| J | (structure: 3,5-dichlorophenyl attached to imidazolidine-2,4-dione with N–C(=O)–NHCH(CH₃)₂ substituent) | 3-(3',5'-Dichlorophenyl)-1-isopropylcarbamoylimidazolidin-2,4-dione |
| K | (structure: 3,5-dichlorophenyl-oxazolidine-2,4-dione with CH=CH₂ and CH₃ substituents at 5-position) | 3-(3',5'-Dichlorophenyl)-5-methyl-5-vinyloxazolidin-2,4-dione |
| L | (structure: 3,5-dichlorophenyl-oxazolidine-2,4-dione with COOC₂H₅ and CH₃ at 5-position) | Ethyl (RS)—3-(3',5'-dichlorophenyl)-5-methyl-2,4-dioxo-oxazolidine-5-carboxylate |

Besides, the compounds (I) may be also used in admixture with other fungicides, herbicides, insecticides, miticides, fertilizers, etc.

When the compounds (I) are used as fungicides, they may be applied in such amounts as 2 to 100 grams per 10 ares. However, this amount may vary depending upon formulation forms, application times, application methods, application sites, diseases, crops and so on, and therefore, they are not limited to said particular amounts.

Some practical embodiments of the fungicidal composition according to the invention are illustratively shown in the following Examples wherein % and part(s) are by weight.

FORMULATION EXAMPLE 1

Two parts of Compound No. 6, 88 parts of clay and 10 parts of talc are thoroughly pulverized and mixed together to obtain a dust formulation containing 2% of the active ingredient.

FORMULATION EXAMPLE 2

Thirty parts of Compond No. 6, 45 parts of diatomaceous earth, 20 parts of white carbon, 3 parts of sodium laurylsulfate as a wetting agent and 2 parts of calcium ligninsulfonate as a dispersing agent are mixed while being powdered to obtain a wettable powder formulation containing 30% of the active ingredient.

FORMULATION EXAMPLE 3

Fifty parts of Compound No. 6, 45 parts of diatomaceous earth, 2.5 parts of calcium alkylbenzenesulfonate as a wetting agent and 2.5 parts of calcium ligninsulfonate as a dispersing agent are mixed while being powdered to obtain a wettable powder formulation containing 50% of the active ingredient.

FORMULATION EXAMPLE 4

Ten parts of Compound No. 6, 80 parts of cyclohexanone and 10 parts of polyoxyethylene alkylaryl ether as an emulsifier are mixed together to obtain an emulsifiable concentrate formulation containing 10% of the active ingredient.

FORMULATION EXAMPLE 5

Eighty parts of Compound No. 6, 10 parts of cyclohexanone and 10 parts of polyoxyethylene alkylaryl ether as an emulsifier are mixed together to obtain an emulsifiable concentrate formulation containing 80% of the active ingredient.

FORMULATION EXAMPLE 6

One part of Compound No. 3, 1 part of Compound I, 88 parts of clay and 10 parts of talc are thoroughly pulverized and mixed together to obtain a dust formulation containing 2 parts of the active ingredient.

FORMULATION EXAMPLE 7

Twenty parts of Compound No. 4, 10 parts of Compound J, 45 parts of diatomaceous earth, 20 parts of white carbon, 3 parts of sodium laurylsulfate as a wetting agent and 2 parts of calcium ligninsulfonate as a dispersing agent are mixed while being powdered to obtain a wettable powder composition containing 30% of the active ingredient.

Formulation Example 8

Ten parts of Compound No. 6, 40 parts of Compound A, 45 parts of diatomaceous earth, 2.5 parts of calcium alkylbenzenesulfonate as a wetting agent and 2.5 parts of calcium ligninsulfonate as a dispersing agent are mixed while being powdered to obtain a wettable powder composition containing 50 % of the active ingredient.

Formulation Example 9

Five parts of Compound No. 3, 5 parts of Compound F, 80 parts of cyclohexanone and 10 parts of polyoxyethylene alkylaryl ether as an emulsifier are mixed together to obtain an emulsifiable concentrate formulation containing 10% of the active ingredient.

Typical test data indicating the excellent fungicidal activity of the compounds (I) are shown below. The compounds used for comparison are as follows:

| Compound | Remarks |
|---|---|
| Swep <br> ![Swep structure: dichlorophenyl-NHCOCH3] | Commercially available herbicide |
| Chlorpropham <br> ![Chlorpropham structure: Cl-phenyl-NHCOOCH(CH3)2] | Commercially available herbicide |
| Barban <br> ![Barban structure: Cl-phenyl-NHCOOCH2C≡CCH2Cl] | Commercially available herbicide |
| CEPC <br> ![CEPC structure: Cl-phenyl-NHCOOCH2CH2Cl] | Commercially available herbicide |
| Propham <br> ![Propham structure: phenyl-NHCOOCH(CH3)2] | Commercially available herbicide |
| Chlorbufam <br> ![Chlorbufam structure: Cl-phenyl-NHCOOCH(C≡CH)CH3] | Commercially available herbicide |
| Benomyl <br> ![Benomyl structure: benzimidazole with CONHC4H9 and NHCOOCH3] | Commercially available fungicide |
| Thiophanate-methyl <br> ![Thiophanate-methyl structure: phenyl with two NHCNHCOOCH3 groups with C=S] | Commercially available fungicide |
| Carbendazim <br> ![Carbendazim structure: benzimidazole-NHCOOCH3] | Commercially available fungicide |
| Thiabendazole <br> 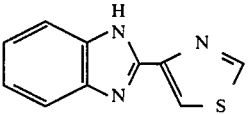 | Commercially available fungicide |

Experiment 1

Protective activity test on powdery mildew of cucumber (*Sphaerotheca fuliginea*):

A flower pot of 90 ml volume was filed with sandy soil, and seeds of cucumber (var: Sagami-hanjiro) were sowed therein. Cultivation was carried out in a greenhouse for 8 days. Onto the resulting seedlings having cotyledons, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Sphaerotheca fuliginea* by spraying and further cultivated in the greenhouse. Ten days thereafter, the infectious state of the plants was observed. The degree of damage was determined in the following manner, and the results are shown in Table 4.

The leaves examined were measured for a percentage of infected area and classified into the corresponding disease indices, 0, 0.5, 1, 2, 4:

| Disease index | Percentage of infected area |
|---|---|
| 0 | No infection |
| 0.5 | Infected area of less than 5% |
| 1 | Infected area of less than 20% |
| 2 | Infected area of less than 50% |
| 4 | Infected area of not less than 50% |

The disease severity was calculated according to the following equation $$\text{Disease severity (\%)} = \frac{\Sigma\{(\text{Disease index}) \times (\text{Number of leaves})\}}{4 \times (\text{Total number of leaves examined})} \times 100$$

The prevention value was calculated according to the following equation:

$$\text{Prevention value (\%)} = 100 - \frac{(\text{Disease severity in treated plot})}{(\text{Disease severity in untreated plot})} \times 100$$

TABLE 4

| Compound No. | Concentration of active ingredient (ppm) | Prevention value when inoculated with drug-resistant strain (%) | Prevention value when inoculated with drug-sensitive strain (%) |
|---|---|---|---|
| 3 | 500 | 100 | 0 |
| 4 | 200 | 100 | 0 |
| 6 | 200 | 100 | 0 |
| Swep | 200 | 0 | 0 |
| Chlorpropham | 200 | 0 | 0 |
| Barban | 200 | 25 | 0 |
| CEPC | 200 | 0 | 0 |
| Propham | 200 | 0 | 0 |
| Chlorbufam | 200 | 0 | 0 |

TABLE 4-continued

| Compound No. | Concentration of active ingredient (ppm) | Prevention value when inoculated with drug-resistant strain (%) | Prevention value when inoculated with drug-sensitive strain (%) |
| --- | --- | --- | --- |
| Benomyl | 200 | 0 | 100 |
| Thiophanate-methyl | 200 | 0 | 100 |
| Carbendazim | 200 | 0 | 100 |

As understood from the results shown in Table 4, the compounds (I) of the invention show an excellent preventive effect on the drug-resistant strain but do not show any preventive effect on the tested drug-sensitive strain To the contrary, commercially available known fungicides such as Benomyl, Thiophanate-methyl and Carbendazim show a notable controlling effect on the drug-sensitive strain but not on the drug-resistant strain. Other tested compounds structurally similar to the compounds (I) do not show any fungicidal activity on the drug-sensitive strain and the drug-resistant strain.

Experiment 2

Preventive effect on cercospora leaf spot of sugarbeet (*Cercospora beticola*):

A flower pot of 90 ml volume was filled with sandy soil, and seeds of sugarbeet (var: Detroit dark red) were sowed therein. Cultivation was carried out in a greenhouse for 20 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Cercospora beticola* by spraying. The pot was covered with a polyvinyl chloride sheet to make a condition of high humidity, and cultivation was continued in the greenhouse for 10 days. The degree of damage was determined in the same manner as in Experiment 1, and the results are shown in Table 5.

TABLE 5

| Compound No. | Concentration of active ingredient (ppm) | Prevention value when inoculated with drug-resistant strain (%) | Prevention value when inoculated with drug-sensitive strain (%) |
| --- | --- | --- | --- |
| 3 | 500 | 100 | 0 |
| 4 | 500 | 100 | 0 |
| 6 | 500 | 100 | 0 |
| Swep | 200 | 0 | 0 |
| Chlorpropham | 200 | 0 | 0 |
| Barban | 200 | 34 | 0 |
| CEPC | 200 | 0 | 0 |
| Propham | 200 | 0 | 0 |
| Chlorbufam | 200 | 0 | 0 |
| Benomyl | 200 | 0 | 100 |
| Thiophanate-methyl | 200 | 0 | 100 |
| Carbendazim | 200 | 0 | 100 |

As understood from the results shown in Table 5, the compounds (I) of the invention show an excellent preventive effect on the drug-resistant strain but do not show any preventive effect on the tested drug-sensitive strain. To the contrary, commecially available known fungicides such as Benomyl and Thiophanate-methyl show a notable controlling effect on the drug-sensitive strain but not on the drug-resistant strain. Other tested compounds structurally similar to the compounds (I) do not show any fungicidal activity on the drug-sensitive strain and the drug-resistant strain.

Experiment 3

Preventive effect on scab of pear (*Venturia nashicola*):

A plastic pot of 90 ml volume was filled with sandy soil, and seeds of pear (var: Chojuro) were sowed therein. Cultivation was carried out in a greenhouse for 20 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Venturia nashicola* by spraying. The resulting plants were placed at 20° C. under a condition of high humidity for 3 days and then at 20° C. under irradiation with a fluorescent lamp for 20 days. The degree of damage was determined in the same manner as in Experiment 1, and the results are shown in Table 6.

TABLE 6

| Compound No. | Concentration of active ingredient (ppm) | Prevention value when inoculated with drug-resistant strain (%) | Prevention value when inoculated with drug-sensitive strain (%) |
| --- | --- | --- | --- |
| 3 | 500 | 100 | 0 |
| 4 | 500 | 100 | 0 |
| 6 | 500 | 100 | 0 |
| Benomyl | 200 | 0 | 100 |
| Thiophanate-methyl | 200 | 0 | 100 |

As understood from the results shown in Table 6, the compounds (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

Experiment 4

Preventive effect on brown leaf-spot of peanut (*Cercospora arachidicola*):

Plastic pots of 90 ml volume was filled with sandy soil, and seeds of peanut (var: Chiba hanryusei) were sowed therein. Cultivation was carried out in a greenhouse for 14 days. Onto the resulting seedlings, the test compound formulated in emulsifiable concentrate or wettable powder and diluted with water was sprayed at a rate of 10 ml per pot. Then, the seedlings were inoculated with a spore suspension of the drug-sensitive strain of *Cercospora arachidicola* by spraying. The resulting plants were covered with a polyvinyl chloride sheet to make a condition of humidity and cultivated in the greenhouse for 10 days. The degree of damage was determined in the same manner as in Experiment 1, and the results are shown in Table 7.

TABLE 7

| Compound No. | Concentration of active ingredient (ppm) | Prevention value when inoculated with drug-resistant strain (%) | Prevention value when inoculated with drug-sensitive strain (%) |
| --- | --- | --- | --- |
| 6 | 500 | 100 | 0 |
| Benomyl | 200 | 0 | 100 |
| Thiophanate- | 200 | 0 | 100 |

TABLE 7-continued

| Compound No. | Concentration of active ingredient (ppm) | Prevention value when inoculated with drug-resistant strain (%) | Prevention value when inoculated with drug-sensitive strain (%) |
| --- | --- | --- | --- |
| methyl | | | |

As understood from the results shown in Table 7, the compounds (I) of the invention show an excellent preventive effect on the drug-resistant strain but do not show any preventive effect on the tested drug-sensitive strain To the contrary, commercially available known fungicides such as Benomyl and Thiophanate-methyl show a notable controlling effect on the drug-sensitive strain but not on the drug-resistant strain.

Experiment 5

Preventive effect on gray mold of cucumber (*Botrytis cinerea*):

Plastic pots of 90 ml volume was filled with sandy soil, and seeds of cucumber (var: Sagami-hanjiro) were sowed therein. Cultivation was carried out in a greenhouse for 8 days to obtain cucumber seedlings expanding cotyle-dons. Onto the resulting seedlings, the test compound formulated in emulsifiable concentrate or wettable powder and diluted with water was sprayed at a rate of 10 ml per pot. After air-drying, the seedlings were inoculated with mycelial disks (5 mm in diameter) of the drug-resistant or drug-sensitive strain of *Botrytis cinerea* by putting them on the leaf surfaces. After the plants were infected by incubating under high humidity at 20° C. for 3 days, the rates of disease severity were observed. The degree of damage was determined in the same manner as in Experiment 1, and the results are shown in Table 8.

TABLE 8

| Compound No. | Concentration of active ingredient (ppm) | Prevention value when inoculated with drug-resistant strain (%) | Prevention value when inoculated with drug-sensitive strain (%) |
| --- | --- | --- | --- |
| 3 | 500 | 100 | 0 |
| 4 | 500 | 100 | 0 |
| 5 | 500 | 100 | 0 |
| 6 | 500 | 100 | 0 |
| Benomyl | 200 | 0 | 100 |
| Thiophanate-methyl | 200 | 0 | 100 |

As understood from the results shown in Table 8, the compounds (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

Experiment 6

Preventive effect on gummy stem blight of cucumber (*Mycosphaerella melonis*):

Plastic pots of 90 ml volume was filled with sandy soil, and seeds of cucumber (var: Sagami-hanjiro) were sowed therein. Cultivation was carried out in a greenhouse for 8 days to obtain cucumber seedlings expanding cotyledons. Onto the resulting seedlings, the test compound formulated in emulsifiable concentrate or wettable powder and diluted with water was sprayed at a rate of 10 ml per pot. After air-drying, the seedlings were inoculated with mycelial disks (5 mm in diameter) of the drug-resistant or drug-sensitive strain of *Mycosphaerella melonis* by putting them on the leaf surfaces. After the plants were infected by incubating under high humidity at 25° C. for 4 days, the rates of disease severity were observed. The degree of damage was determined in the same manner as in Experiment 1, and the results are shown in Table 9.

TABLE 9

| Compound No. | Concentration of active ingredient (ppm) | Prevention value when inoculated with drug-resistant strain (%) | Prevention value when inoculated with drug-sensitive strain (%) |
| --- | --- | --- | --- |
| 3 | 500 | 100 | 0 |
| 4 | 500 | 100 | 0 |
| 6 | 500 | 100 | 0 |
| Benomyl | 200 | 0 | 100 |
| Thiophanate-methyl | 200 | 0 | 100 |

As understood from the results shown in Table 9, the compounds (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

Experiment 7

Preventive effect on green mold of orange (*Penicillium italicum*): Fruits of orange (var: Unshu) were washed with water and dried in the air. The fruits were immersed in a solution of the test compound prepared by diluting an emulsifiable concentrate comprising the test compound with water for 1 minute. After drying in the air, the fruits were inoculated with a spore suspension of the drug-resistant or drug-sensitive strain of *Penicillium italicum* by spraying and placed in a room of high humidity for 14 days. The degree of damage was determined in the following manner:

The fruits examined were measured for a percentage of infected area and classified into the corresponding indices, 0, 1, 2, 3, 4, 5:

| Disease index | Percentage of infected area |
| --- | --- |
| 0 | No infection |
| 1 | Infected area of less than 20% |
| 2 | Infected area of less than 40% |
| 3 | Infected area of less than 60% |
| 4 | Infected area of less than 80% |
| 5 | Infected area of not less than 80% |

Calculation of the degree of damage and the prevention value was made as in Experiment 1. The results are shown in Table 10.

TABLE 10

| Compound No. | Concentraton of active ingredient (ppm) | Prevention value when inoculated with drug-resistant strain (%) | Prevention value when inoculated with drug-sensitive strain (%) |
| --- | --- | --- | --- |
| 6 | 500 | 100 | 0 |
| Benomyl | 200 | 0 | 100 |
| Thiophanate- | 200 | 0 | 100 |

TABLE 10-continued

| Compound No. | Concentraton of active ingredient (ppm) | Prevention value when inoculated with drug-resistant strain (%) | Prevention value when inoculated with drug-sensitive strain (%) |
| --- | --- | --- | --- |
| methyl | | | |

As understood from the results shown in Table 10, the compounds (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

Experiment 8

Phytotoxicity on crop plants:

Plastic pots of 150 ml volume were filled with sandy soil, and seeds of wheat (var: Norin No. 61), apple (var: Kogyoku) and peanut (var: Chiba hanryusei) were sowed therein. Cultivation was carried out in a greenhouse. Onto the resulting seedlings, the test compound formulated in emulsifiable concentrate or wettable powder and diluted with water was sprayed. After cultivation in the greenhouse for additional 10 days, the phytotoxicity was examined on the following criteria:

| Extent | Observation |
| --- | --- |
| − | No abnormality |
| + | Abnormality due to phytotoxicity observed in a part of crop plants |
| ++ | Abnormality due to phytotoxicity observed in entire crop plants |
| +++ | Crop plants withered due to phytotoxicity |

The results are shown in Table 11.

TABLE 11

| Compound No. | Concentration of active ingredient (ppm) | Phytotoxicity Wheat | Apple | Peanut |
| --- | --- | --- | --- | --- |
| 6 | 1000 | − | − | − |
| Barban | 1000 | − | ++ | ++ |
| CEPC | 1000 | − | ++ | ++ |
| Swep | 1000 | ++ | ++ | + |

As understood from the results shown in Table 11, the compounds of the formula (I) of the invention produce no material phytotoxicity, while commercially available herbicides having a chemical structure similar thereto produce considerable phytotoxicity.

Experiment 9

Preventive effect on powdery mildew of cucumber (Sphaerotheca fuliginea):

A plastic pot of 90 ml volume was filled with sandy soil, and seeds of cucumber (var: Sagami-hanjiro) were sowed therein. Cultivation was carried out in a greenhouse for 8 days. Onto the resulting seedings having cotyledons, the test compound(s) formulated in emulsifiable concentrate or wettable powder and diluted with water were sprayed at a rate of 10 ml per pot. Then, the seedlings were inoculated with a mixed spore suspension of the drug-resistant and drug-sensitive strain of Spuhaerotheca fuliginea by spraying and further cultivated in the greenhouse. Ten days thereafter, the infectious state of the plants was observed. The degree of damage was determined in the same manner as in Experiment 1, and the results are shown in Table 12.

TABLE 12

| Compound No. | Concentration of active ingredient (ppm) | Prevention value (%) |
| --- | --- | --- |
| 3 | 100 | 38 |
| 3 | 20 | 0 |
| 4 | 100 | 42 |
| 4 | 20 | 0 |
| 6 | 100 | 40 |
| 6 | 20 | 0 |
| A | 100 | 43 |
| A | 20 | 10 |
| B | 500 | 44 |
| B | 100 | 8 |
| C | 100 | 46 |
| C | 20 | 10 |
| D | 500 | 34 |
| D | 100 | 0 |
| E | 100 | 45 |
| E | 20 | 8 |
| F | 100 | 42 |
| F | 20 | 8 |
| G | 100 | 42 |
| G | 20 | 10 |
| H | 100 | 42 |
| H | 20 | 8 |
| 3 + A | 20 + 20 | 100 |
| 3 + F | 20 + 20 | 100 |
| 4 + A | 20 + 20 | 100 |
| 4 + B | 20 + 20 | 100 |
| 4 + C | 20 + 20 | 100 |
| 4 + D | 20 + 20 | 100 |
| 4 + G | 20 + 20 | 100 |
| 4 + H | 20 + 20 | 100 |
| 6 + A | 20 + 20 | 100 |
| 6 + B | 20 + 20 | 100 |
| 6 + E | 20 + 20 | 100 |

As understood from the results shown in Table 12, the combined use of the compounds (I) of the invention with benzimidazole thiophanate fungicides and/or cyclic imide fungicides show much more excellent preventive effect than their sole use.

Experiment 10 l preventive effect on gray mold of tomato (Botrytis cinerea):

A plastic pot of 90 ml volume was filled with sandy soil, and seeds of tomato (var: Fukuju No. 2) were sowed therein. Cultivation was carried out in a greenhouse for 4 weeks. Onto the resulting seedlings at the 4-leaf stage, the test compound(s) formulated in emulsifiable concentrate or wettable powder and diluted with water were sprayed at a rate of 10 ml per pot. Then, the seedlings were inoculated with a mixed spore suspension of the drug-resistant and drug sensitive strain of Botrytis cinerea by spraying and placed at 20° C. in a room of high humidity for 5 days. The degree of damage was determined in the same manner as in Experiment 1, and the results are shown in Table 13.

TABLE 13

| Compound No. | Concentration of active ingredient (ppm) | Prevention value (%) |
| --- | --- | --- |
| 3 | 100 | 34 |
| 3 | 20 | 0 |
| 4 | 100 | 32 |
| 4 | 20 | 0 |
| 6 | 100 | 34 |
| 6 | 20 | 0 |
| I | 100 | 48 |

TABLE 13-continued

| Compound No. | Concentration of active ingredient (ppm) | Prevention value (%) |
| --- | --- | --- |
| I | 20 | 20 |
| J | 500 | 44 |
| J | 100 | 16 |
| K | 100 | 40 |
| K | 20 | 18 |
| L | 500 | 42 |
| L | 100 | 10 |
| 3 + I | 10 + 20 | 100 |
| 3 + J | 10 + 20 | 100 |
| 3 + K | 10 + 20 | 100 |
| 3 + L | 10 + 20 | 100 |
| 4 + I | 10 + 20 | 100 |
| 4 + K | 10 + 20 | 100 |
| 6 + I | 10 + 20 | 100 |
| 6 + L | 10 + 20 | 100 |

As understood from the results shown in Table 13, the combined use of the compounds (I) of the invention with benzimidazole or thiophanate fungicides and/or cyclic imide fungicides show much more excellent preventive effect than their sole use.

What is claimed is:

1. A compound of the formula:

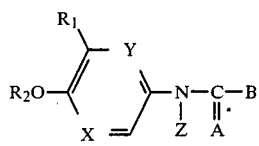

wherein
either one of X and Y is a methine group and the other is a nitrogen atom;
$R_1$ is a halogen atom or a group of the formula: —$WR_3$ or —$NHCOOR_4$ in which W is an oxygen atom or a sulfur atom, $R_3$ is a lower alkyl group, a lower alkenyl group, a lower alkynyl group, a lower haloalkyl group or a lower alkoxy(lower)alkyl group and $R_4$ is a lower alkyl group provided that —$WR_3$ is not —$OCH_3$;
$R_2$ is a lower alkyl group other than methyl, a lower alkenyl group, a lower alkynyl group, a lower haloalkyl group or a lower alkoxy(lower)alkyl group;
Z is a hydrogen atom, a lower alkyl group, a lower alkenyl group, a lower alkynyl group, a lower alkoxycarbonyl-(lower)alkyl group or a group of the formula: —$COR_5$ or —$SR_6$ in which $R_5$ is a lower alkyl group, a cyclo(lower)-alkyl group or a phenyl group and $R_6$ is a lower alkyl group, a phenyl group or a lower alkoxycarbonyl group;
A is an oxygen atom or a sulfur atom; and
B is a lower alkyl group, a lower alkenyl group, a cyclo(lower)alkyl group, a phenyl group or a group of the formula: $W'R_7$ in which $W'$ is an oxygen atom or a sulfur atom and $R_7$ is a lower alkyl group, a lower alkenyl group, a lower alkynyl group, a halo(lower)alkenyl group, a halo-(lower)alkynyl group, a cyclo(lower)alkyl group, a phenyl group optionally substituted with halogen or a lower alkyl group substituted with at least one member selected from the group consisting of halogen, cyano, phenyl, cyclo(lower)-alkyl or lower alkoxy.

2. The compound according to claim 1, wherein X is a methine group, Y is a nitrogen atom, Z is a hydrogen atom, A is an oxygen atom, B is a lower alkyl group, a lower cycloalkyl group or a group of the formula: —$WR_3$ in which W is an oxygen atom or a sulfur atom and $R_3$ is a lower alkyl group or a lower alkenyl group, $R_1$ is a lower alkoxy group and $R_2$ is a lower alkyl group.

3. The compound according to claim 1, wherein X is a methine group, Y is a nitrogen atom, Z is a hydrogen atom, A is an oxygen atom, B is an ethyl group, a cyclopropyl group, an ethylthio group or a group of the formula: —$OR3$ in which $R_3$ is a methyl group, an ethyl group, an isopropyl group or an allyl group, $R_1$ is an ethoxy group and $R_2$ is an ethyl group.

4. The compound of claim 1 which is:

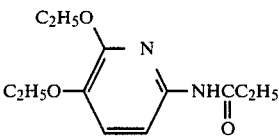

5. The compound of claim 1 which is:

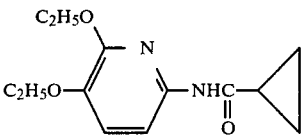

6. A fungicidal composition which comprises as an active ingredient a fungicidally effective amount of a compound of the formula:

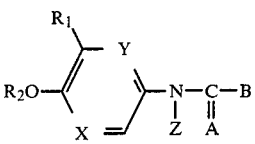

wherein
either one of X and Y is a methine group and the other is a nitrogen atom;
$R_1$ is a halogen atom or a group of the formula: —$WR3$ or —$NHCOOR_4$ in which W is an oxygen atom or a sulfur atom, $R_3$ is a lower alkyl group, a lower alkenyl group, a lower alkynyl group, a lower haloalkyl group or a lower alkoxy(lower)alkyl group and $R_4$ is a lower alkyl group provided that $WR_3$ is not —$OCH_3$;
$R_2$ is a lower alkyl group other than methyl, a lower alkenyl group, a lower haloalkyl group or a lower alkoxy(lower)alkyl group;
Z is a hydrogen atom, a lower alkyl group, a lower alkenyl group, a lower alkynyl group, a lower alkoxycarbonyl-(lower)alkyl group or a group of the formula: —$COR_5$ or —$SR_6$ in which $R_5$ is a lower alkyl group, a cyclo(lower)alkyl group or a phenyl group and $R_6$ is a lower alkyl group, a phenyl group or a lower alkoxycarbonyl group;
A is an oxygen atom or a sulfur atom; and
B is a lower alkyl group, a lower alkenyl group, a cyclo(lower)akyl group, a phenyl group or a group of the formula: —$W'R_7$ in which $W'$ is an oxygen atom or a sulfur atom and $R_7$ is a lower alkyl group, a lower alkenyl group, a lower alkynyl group, halo(lower)alkenyl group, a halo-(lower)alkynyl group, a cyclo(lower)alkyl group, a phenyl group optionally substituted with halogen or a lower alkyl group substituted with at least one member selected from the group consisting of halogen, cyano, phenyl, cyclo(lower)-alkyl or lower alkoxy, and an inert carrier or diluent.

7. The fungicidal composition according to claim 6, which further comprises as an additional active ingredient(s) a benzimidazole or thiophanate fungicide and/or a cyclic imide fungicide.

8. The fungicidal composition according to claim 7, wherein the benzimidazole or thiophanate fungicide is methyl 1-(butylcarbamoyl)benzimidazol-2-ylcarbamate, 2-(2-furyl)benzimidazole, 2-(4-thiazolyl)benzimidazole, methyl benzimidazol-2-ylcarbamate, 1,2-bis(3-methoxycarbonyl-2-thioureido)benzene, 1,2-bis(3-ethoxycarbonyl-2-thioureido)-benzene, 2-(O,S-dimethylphosphorylamino)-1-(3'-methoxycarbonyl-2'-thioureido)-benzene or 2-(0,0-dimethylthiophos-phorylamino)-1-(3'-methoxycarbonyl-2'-thioureido)benzene and the cyclic imide fungicide is N-(3',5'-dichlorophenyl)-1,2-dimethylcyclopropane-1,2-dicarboximide, 3-(3', 5'-dichlorophenyl-1-isopropylcarbamoylimidazolidine-2,4-dione, 3-(3', 5'-dichlorophenyl)-5-methyl-5-vinyloxazoline-2,4-dione or ethyl (RS)-3-(3', 5'-dichlorophenyl)-5-methyl-2,4-dioxooxazolidine-5-carboxylate.

9. A method for controlling plant pathogenic fungi which comprises applying a fungicidally effective amount of at least one of the compounds of the formula:

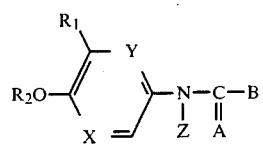

wherein X, Y, Z, A, B, $R_1$ and $R_2$ are each as defined in claim 1, to plant pathogenic fungi.

10. The method according to claim 7, wherein the plant pathogenic fungi is a drug-resistant strain.

11. A method for controlling plant pathogenic fungi which comprises applying a fungicidally effective amount of a mixture of the compound of the formula:

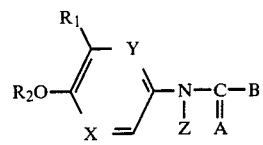

wherein X, Y, Z, A, B, $R_1$ and $R_2$ are each as defined in claim 1 and a benzimidazole or thiophanate fungicide and/or a cyclic imide fungicide.

* * * * *